United States Patent [19]

Gallati et al.

[11] Patent Number: 4,467,031

[45] Date of Patent: Aug. 21, 1984

[54] ENZYME-IMMUNOASSAY FOR CARCINOEMBRYONIC ANTIGEN

[75] Inventors: Harald Gallati, Dornach; Hans Brodbeck, Münchenstein, both of Switzerland

[73] Assignee: Hoffmann-La Roche Inc., Nutley, N.J.

[21] Appl. No.: 408,388

[22] Filed: Aug. 16, 1982

[30] Foreign Application Priority Data

Aug. 21, 1981 [CH] Switzerland .......................... 5403/81
Nov. 11, 1981 [CH] Switzerland .......................... 7258/81

[51] Int. Cl.³ ............................................ G01N 33/54
[52] U.S. Cl. .......................................... 435/7; 422/61;
    435/810; 436/548; 436/813; 436/826
[58] Field of Search .................. 436/813, 548, 826; 435/7, 810; 422/61

[56] References Cited

U.S. PATENT DOCUMENTS 4,180,556 12/1979 Kim .
4,272,504  6/1981 Kim ................................ 436/813 X
4,299,815 11/1981 Hansen ........................... 436/813 X
4,376,110  3/1983 David .............................. 435/7 X

FOREIGN PATENT DOCUMENTS

EP095271 11/1979 European Pat. Off. .
WO81/01469 5/1981 PCT Int'l Appl. .
1549069  7/1979 United Kingdom .

*Primary Examiner*—Sidney Marantz
*Attorney, Agent, or Firm*—Jon S. Saxe; George M. Gould; John J. Maitner

[57] ABSTRACT

A solid phase-sandwich enzyme-immunoassay method for the rapid determination of carcinoembryonic antigen (CEA). The sample to be investigated is incubated with a first CEA antibody, which is bound to a water-insoluble carrier, and a second CEA antibody, to which peroxidase is bound directly or via a biotin/avidin bridge. The immunological reaction can be carried out in one or two steps. By the presence of 0.4–1.0 mol/l of phosphate ions, 0.3–0.4 mol/l of sulfate ions or 0.2–0.4 mol/l of tartrate ions in the immunological reaction or in the second step thereof (insofar as it is carried out in two steps) the incubation time period is shortened considerably. After the immunological reaction, the phases are separated, whereupon the peroxidase activity is measured either in the solid or in the liquid phase as the amount of CEA present in the sample.

16 Claims, No Drawings

ENZYME-IMMUNOASSAY FOR CARCINOEMBRYONIC ANTIGEN

BACKGROUND OF THE INVENTION

An enzyme-immunoassay for the determination of carcinoembryonic antigen (CEA) is described by Maiolini et al., in Clinical Chemistry 26/12, 1718–1722 (1980). According to this assay, pre-treated serum or plasma samples are incubated in a first step for two hours at 45° C. with beads which are sensitized with guinea pig-anti-CEA. After a washing step, the beads are incubated for two hours at 45° C. with a conjugate of goat-anti-CEA and horseradish peroxidase. After removing excess conjugate by washing, the enzyme activity is determined on the solid phase according to known methods. By comparing this value with a standard curve prepared in an analogous manner the content of CEA in the sample is ascertained.

The above noted enzyme-immunoassay method for the determination of antigens, in the present case of CEA, is generally known as the so-called solid phase-sandwich method.

It is a primary object of the present invention to provide a method for carrying out the enzyme-immunoassay without the time-consuming and laborious washing step between the first and the second immunological reactions without loss of sensitivity and in the same time-span.

Furthermore, it has been found that by using the process of the present invention, the two-step method in accordance with Clinical Chemistry (loc.cit.) can also be shortened in time, in that the second incubation can be carried out without loss of sensitivity in half the time, i.e. in one hour.

DETAILED DESCRIPTION OF THE INVENTION

The present invention is directed to a solid phase-sandwich method for the rapid determination of carcinoembryonic antigen (CEA) by incubating the sample to be investigated with a first CEA antibody, which is bound to or becomes bound to a water-insoluble carrier, and a second CEA antibody, to which peroxidase is bound directly or via a biotin/avidin bridge, separating the solid and liquid phase and measuring the peroxidase activity either in the solid or liquid phase as the amount of CEA present, which method comprises carrying out the incubation in the presence of 0.4–1.0 mol/l of phosphate ions, of 0.2–0.4 mol/l of sulfate ions or of 0.2–0.4 mol/l of tartrate ions.

According to the solid phase-sandwich method of the present invention, the sample to be investigated can be incubated with the one CEA antibody, which is bound to a water-insoluble carrier, and subsequently, after a washing step, with the second CEA antibody, which is labelled with peroxidase. Since the activating effect of 0.4–1.0 mol/l of phosphate ions, of 0.2–0.4 mol/l of sulfate ions or of 0.2–0.4 mol/l of tartrate ions has an effect on the second incubation, this second incubation is accordingly carried out in the presence of these ions.

As the first CEA antibody, which is bound to a water-insoluble carrier, there can be used a guinea pig-CEA antibody. As the second CEA-antibody, to which is bound peroxidase, there can be used goat-anti-CEA.

In addition to the first and second CEA-antibodies mentioned above, two different monoclonal mouse-CEA antibodies, which are both directed against CEA, but which are directed against different epitopes of CEA, can also be used in carrying out the assay of the present invention.

Furthermore, it is also possible to use as the first antibody a monoclonal mouse-CEA antibody and as the second antibody a polyclonal antibody from an antiserum of an animal, e.g. of the goat.

The peroxidase can be bound to the antibody according to known methods, for example the method Wilson and Nakane described in "Immunofluorescence and Related Staining Techniques", 1978, page 215. In the case of the monoclonal mouse-CEA antibodies, it has been found that in these prior art methods the immunological properties of these antibodies are impaired under certain circumstances. In these cases, it is advantageous to biotinylate the monoclonal mouse-CEA antibody and subsequently to react the product with an avidin-peroxidase complex. The preparation of the avidin-peroxidase complex is carried out in an analogous manner to the method of Wilson and Nakane mentioned above. In the case of polyclonal antibodies, i.e. antibodies from animal serum, the direct binding of the peroxidase to the antibody is preferred.

Examples of water-insoluble carriers for the first antibody are: organic and inorganic polymers, for example, amylase, dextran, natural or modified cellulose, polyacrylamide, agarose, magnetite, porous glass powder, polyvinylidene fluoride (Kynar), latex and the like; the interior wall of test vessels, for example, test tubes, titre plates or cuvettes of glass or synthetic material, as well as the surface of solid bodies, for example, rods, beads or other bodies of glass or synthetic material. Beads of glass and synthetic material are especially suitable carriers for the method in accordance with the invention.

The antibody can be bound to the water-insoluble carrier during or after the reaction. Binding of the antibody to the water-insoluble carrier can be physically (adsorptively) or chemically or with the aid of a further reaction partner which, in turn, is bound to a carrier.

The immunological reactions are preferably carried out at a temperature between 0° and 55° C. The rate of reaction for the immunological reaction normally increases with higher temperatures, whereby under otherwise similar test conditions the equilibrium is achieved more rapidly.

The novel method of the present invention is extraordinarily sensitive and is distinguished in particular by its short reaction time.

A test kit for the method in accordance with the invention comprises especially a container with CEA antibodies, to which is coupled peroxidase, in an aqueous solution of pH 4–9, which contains 0.4–1.0 mol/l of phosphate ions, 0.2–0.4 mol/l of sulfate ions or 0.2–0.4 mol/l of tartrate ions.

Examples of salts which give rise to the phosphate, sulfate and tartrate ions, in the presence of which the instant incubation is carried out, are the respective alkali metal salts, such as sodium and potassium salts, i.e. sodium and potassium phosphate, sulfate and tartrate.

The following Examples illustrate the invention:

EXAMPLE 1

Quantitative determination of CEA in plasma of patients with monoclonal CEA antibody and a customary CEA antibody (goat)

Into the requisite number of test tubes (10×75 mm) there is in each case pipetted 0.2 ml of test solution (0.8 mol/l of $NaH_2PO_4/Na_2HPO_4$, pH 6.5, with 2 g/l of bovine serum albumin, 20% of normal goat serum, 0.2 g/l of 4-amino-antipyrine and 0.2 μg/ml of goat-anti-CEA-peroxidase conjugate), 0.050 ml of the patient's plasma to be analyzed or of the CEA standard (0 ng ml of CEA, 2.5 ng/ml of CEA, 10 ng/ml of CEA and 20 ng/ml of CEA) and of the CEA control serum (10.2 ng/ml of CEA±1.0 ng/ml) is admixed, in each case there is added a polystyrene bead sensitized with monoclonal mouse-anti-CEA* ($\phi=6.5$ mm) and the mixture is incubated at 45° C. for 4 hours. The polystyrene beads are subsequently washed three times with 2-5 ml of distilled water each time, transferred into in each case 0.5 ml of substrate buffer in order to determine the activity of the peroxidase (0.1 mol/l of potassium citrate buffer of pH 5.0 with 6 mmol/l of $H_2O_2$ and 40 mmol/l of o-phenylenediamine) and incubated at room temperature (22° C.) for 30 minutes. In order to stop the peroxidative activity and to enhance the color intensity, 2.0 ml of 1 mol/l HCl are admixed and within 30 minutes the absorption is measured photometrically at the wavelength 492 nm. Table I hereinafter contains the values of a CEA determination and a comparison of these values with on the one hand the values obtained with the radioimmunoassay of ROCHE (reference values) (cf. Clin. Res. 19 (1971), 143) and on the other hand with the values obtained according to a modified method in accordance with Clin. Chem. 26/12, 1718–1722 (1980) (use of a goat anti-CEA-peroxidase conjugate in 0.2M phosphate buffer in place of TRIS buffer).

*The preparation of the monoclonal mouse-anti-CEA is carried out in an analogous manner to the method described in Journal of Immunological Methods, 32 (1980) 297–304, there being used as the starting cell line for the fusion the myeloma line Sp 2/01-AG, which was deposited with ATCC under No CRL 8006 on May 25, 1979 and which was made unconditionally accessible to the public on Nov. 24, 1981. The fusion is carried out with spleen cells of mice which have been immunized with CEA. The immunization of the mice was carried out in analogy to Table I of the aforementioned publication, the first two immunizations being carried out with in each case 50 μg of CEA, immunizations 3 and 4 being omitted, immunization 5 being carried out with 50 μg of CEA and immunizations 6–8 being carried out with in each case 200 μg of CEA.

TABLE I

| Sample material | $\Delta A_{492}$ nm/RT/30 min. | |
|---|---|---|
| CEA standard | | |
| 0 ng/ml CEA | 0.105 | |
| 2.5 ng/ml CEA | 0.330 | |
| 5.0 ng/ml CEA | 0.490 | |
| 10.0 ng/ml CEA | 0.755 | |
| 20.0 ng/ml CEA | 1.220 | |
| CEA control serum | | |
| 10.2 ng/ml CEA | 0.770 | |

| Patient's plasma | ROCHE$^R$RIA test* amount of CEA | Modified method according to Clin. Chem. (loc. cit.) amount of CEA | Method in accordance with the invention amount of CEA |
|---|---|---|---|
| No. pool 1 | 0.8 ng/ml | 0.7 ng/ml | 0.7 ng/ml |
| No. pool 2 | 1.4 ng/ml | 1.0 ng/ml | 1.0 ng/ml |
| No. pool 3 | 2.3 ng/ml | 2.5 ng/ml | 2.4 ng/ml |
| No. 3155 | 25.0 ng/ml | 20.0 ng/ml | 22.0 ng/ml |
| No. 3157 | 3.3 ng/ml | 4.1 ng/ml | 3.7 ng/ml |
| No. 3368 | 7.1 ng/ml | 6.7 ng/ml | 6.9 ng/ml |
| No. 3395 | 14.8 ng/ml | 15.0 ng/ml | 14.7 ng/ml |
| No. 3401 | 9.0 ng/ml | 8.8 ng/ml | 9.2 ng/ml |
| No. 3410 | 23.0 ng/ml | 21.0 ng/ml | 24.0 ng/ml |
| No. 3419 | 4.2 ng/ml | 4.5 ng/ml | 4.4 ng/ml |
| No. 3416 | 4.1 ng/ml | 5.3 ng/ml | 5.2 ng/ml |
| No. 3646 | 5.5 ng/ml | 5.2 ng/ml | 5.3 ng/ml |
| No. 3657 | 5.2 ng/ml | 5.5 ng/ml | 5.5 ng/ml |
| No. 3679 | 5.7 ng/ml | 5.9 ng/ml | 6.0 ng/ml |

*(cf. Clin. Res. 19 (1971), 143)

Values below 2.5 ng/ml of CEA lie in the normal range, while values above 2.5 ng/ml lie in the pathological range. From Table I it is evident that the values obtained with the method in accordance with the invention correlate well with those values obtained according to the modified method in Clin. Chem. (loc.cit.) or according to the ROCHE RIA test.

EXAMPLE 2

Enhancement in sensitivity of the enzyme-immunological CEA determination with a monoclonal mouse-anti-CEA and a goat-anti-CEA-peroxidase conjugate by the addition of 0.8 mol/l of phosphate ions Into the requisite number of test tubes (10×75 mm) there is in each case pipetted 0.2 ml of test solution (2 g/l of bovine serum albumin, 20% of goat serum, 0.2 g/l of 4-amino-antipyrine and 0.2 μg/ml of goat-anti-CEA-peroxidase conjugate in one case in 0.2 mol/l of sodium phosphate buffer and in one case in 0.8 mol/l of sodium phosphate buffer of pH 6.5), 0.050 ml of the CEA standard (0 ng/ml of CEA, 2.5 ng/ml of CEA, 5.0 ng/ml of CEA, 10.0 ng/ml of CEA and 20.0 ng/ml of CEA) and of the CEA control serum (10.2 ng/ml of CEA±1.0 ng/ml) is admixed, in each case there is added a polystyrene bead ($\phi=6.5$ mm) sensitized with monoclonal mouse-CEA antibody and the mixture is incubated at 45° C. for 4 hours. The polystyrene beads are subsequently washed three times with in each case 2–5 ml of distilled water, transferred into in each case 0.5 ml of substrate buffer in order to determine the activity of the peroxidase (0.1 mol/l of potassium citrate of pH 5.0 with 6 mmol/l of $H_2O_2$ and 40 mmol/l of o-phenylenediamine) and incubated at room temperature (22° C.) for 30 minutes. In order to stop the peroxidative activity and to enhance the color intensity, 2.0 ml of 1 mol/l HCl are admixed with within 30 minutes to absorption is measured photometrically at the wavelength 492 mm. Table II hereinafter contains the values obtained with 0.2 mol/l and 0.8 mol/l of sodium phosphate buffer.

TABLE II

| | $\Delta A_{492}$ nm/RT/30 min. | |
|---|---|---|
| | With 0.2 mol/l of phosphate ions | With 0.8 mol/l of phosphate ions |
| CEA standards | | |
| 0 ng/ml CEA | 0.050 | 0.130 |
| 2.5 ng/ml CEA | 0.125 | 0.290 |
| 5.0 ng/ml CEA | 0.230 | 0.450 |
| 10.0 ng/ml CEA | 0.400 | 0.770 |
| 20.0 ng/ml CEA | 0.780 | 1.400 |
| CEA control serum | | |
| 10.2 ng/ml CEA | 0.430 | 0.800 |

From Table II it is clearly evident that the sensitivity is clearly enhanced with the use of 0.8 mol/l of phosphate ions compared with 0.2 mol/l of phosphate ions.

EXAMPLE 3

Enhancement in sensitivity of the enzyme-immunological CEA determination with a monoclonal mouse-anti-CEA and a goat-anti-CEA-peroxidase conjugate by the addition of 0.4 mol/l of sulfate ions Into the requisite number of test tubes (10×75 mm) there is in each case pipetted 0.2 ml of test solution (2 g/l of bovine serum albumin, 20% of goat serum, 0.2 g/l of 4-amino-antipyrine and 0.2 µg/ml of goat-anti-CEA-peroxidase conjugate in 0.2 mol/l of sodium phosphate buffer in one case without sulfate ions and in one case with 0.4 mol/l of sulfate ions ($Na_2SO_4$) of pH value 6.5), 0.050 ml of the CEA standard (0 ng/ml of CEA, 2.5 ng/ml of CEA, 5.0 ng/ml of CEA, 10.0 ng/ml of CEA and 20.0 ng/ml of CEA) and of the CEA control serum (10.2 ng/ml of CEA±1.0 ng/ml) is admixed, in each case there is added a polystyrene bead ($\phi=6.5$ mm) sensitized with monoclonal mouse-CEA antibody and the mixture is incubated at 45° C. for 4 hours. The polystyrene beads are subsequently washed three times with in each case 2–5 ml of distilled water, transferred into in each case 0.5 ml of substrate buffer in order to determine the activity of the peroxidase (0.1 mol/l of potassium citrate of pH 5.0 with 6 mmol/l of $H_2O$ and 40 mmol/l of o-phenylenediamine) and incubated at room temperature (22° C.) for 30 minutes. In order to stop the peroxidative activity and to enhance the color intensity, 2.0 ml of a 1 mol/l HCl are admixed and within 30 minutes with absorption is measured photometrically at the wavelength 492 nm. Table III hereinafter contains the values obtained with 0.2 mol/l of sodium phosphate buffer in one case without sulfate ions and in one case with 0.4 mol/l of sulfate ions.

TABLE III

| | $\Delta A_{492}$ nm/RT/30 min. | |
|---|---|---|
| | Without sulfate ions | With 0.4 mol/l of sulfate ions |
| CEA standard | | |
| 0 ng/ml CEA | 0.050 | 0.135 |
| 2.5 ng/ml CEA | 0.125 | 0.350 |
| 5.0 ng/ml CEA | 0.230 | 0.520 |
| 10.0 ng/ml CEA | 0.400 | 0.890 |
| 20.0 ng/ml CEA | 0.780 | 1.620 |
| CEA control serum | | |
| 10.2 ng/ml CEA | 0.430 | 0.930 |

From Table III it is clearly evident that the sensitivity is enhanced considered by the presence of the sulfate ions.

EXAMPLE 4

Enhancement of the test sensitivity by increased phosphate concentration when using monoclonal, biotinylated anti-CEA and avidin-peroxidase complex Into the requisite number of test tubes (10×75 mm) there is in each case pipetted 0.2 ml of test solution [0.2 mol/l or 0.8 mol/l of sodium phosphate buffer of pH 6.5 with 2 g/l of bovine serum albumin, 20% of goat serum, 0.1 g/l of 4-amino-antipyrine and 480 ng/ml of monoclonal mouse anti-CEA-(C-3)-biotin/avidin-peroxidase]. With this test solution there is admixed 0.050 ml of the CEA standard (0 ng/ml of CEA, 2.5 ng/ml of CEA, 5.0 ng/ml of CEA, 10 ng/ml of CEA and 20 ng/ml of CEA), in each case there is added a polystyrene bead ($\phi=6.5$ mm) sensitized with monoclonal mouse anti-CEA-(C-19) and the mixture is incubated at 37° C. for 16 hours. The polystyrene beads are subsequently washed three times with in each case 2–5 ml of distilled water, transferred into in each case 0.5 ml of substrate buffer (0.1 mol/l of potassium citrate of pH 5.0 with 6 mmol/l of $H_2O_2$ and 40 mmol/l of o-phenylenediamine) in order to determine the activity of the peroxidase immunologically bound to the bead and incubated at 18°–26° C. for 30 minutes. In order to stop the peroxidative activity and to enhance the color intensity, 2.0 ml of 1N HCl are admixed and within 30 minutes the extinction is measured photometrically at the wavelength 492 nm. Table IV hereinafter contains the values for the CEA standards.

TABLE IV

| | $\Delta E_{492}$ nm/20° C./30 min. | |
|---|---|---|
| CEA standard | 0.2 mol/l phosphate buffer | 0.8 mol/l phosphate buffer |
| 0 ng/ml CEA | 0.080/0.080 | 0.090/0.095 |
| 2.5 ng/ml CEA | 0.160/0.170 | 0.310/0.315 |
| 5.0 ng/ml CEA | 0.230/0.235 | 0.450/0.460 |
| 10 ng/ml CEA | 0.425/0.435 | 0.830/0.850 |
| 20 ng/ml CEA | 0.810/0.825 | 1.700/1.650 |

From Table IV it is clearly evident that the sensitivity is enhanced considerably by increased phosphate concentration.

The monoclonal mouse-anti-CEA antibodies used in this Example are obtained in analogy to the method described by Stahli et al. in Journal of Immunological Methods, 32 (1980) 297–304, but using as the starting cell line for the fusion the aforementioned myeloma line Sp 2/01-AG. The fusion is carried out with spleen cells of mice which have been immunized with CEA. The immunization of the mice was carried out in analogy to Table I of the aforementioned publication, the first two immunizations being carried out with in each case 50 µg of CEA, immunizations 3 and 4 being omitted, immunization 5 being carried out with 50 µg of CEA and immunizations 6–8 being carried out with in each case 200 µg of CEA. There are used two different, suitable monoclonal antibodies which are directed against different epitopes of the CEA antigen and which are denoted as anti-CEA (C-3) and anti-CEA (C-19), respectively.

The IgG fraction of anti-CEA (C-3) antibodies is dialyzed overnight at 2°–8° C. against 0.1 mol/l sodium bicarbonate solution (pH 8.2–8.5) and adjusted to a protein concentration of 1 mg/ml. Therewith there are admixed per ml of protein solution 120 µl of a completely freshly prepared biotin succinimide ester solution (1 mg/ml in dimethyl sulfoxide and the mixture is incubated at room temperature for 4 hours. The biotin-antibody conjugate is subsequently dialyzed at 2°–8° C. against phosphate-buffered physiological sodium chloride solution with 0.66 mg/l of Merfen. 10 mg/ml of bovine serum albumin are admixed as the protein stabilizer.

In order to couple peroxidase to avidin, 5 mg of avidin are dissolved in 2.5 ml of a 0.1 mol/l sodium bicarbonate solution (pH 9.5) and dialyzed overnight at 2°–8° C. against the same solution. 10 mg of peroxidase from horseradish are dissolved in 3.0 ml of distilled water, left to stand at room temperature for 1 hour, then mixed with 0.5 ml of an aqueous freshly prepared 0.1 mol/l sodium periodate solution and incubated at room temperature for exactly 20 minutes. The peroxidase is then freed from excess sodium periodate by ultrafiltration and concentrated to the original volume. After ultrafiltration, the peroxidase solution is admixed with the avidin solution, whereupon the mixture is incubated at room temperature for 2 hours. In order to reduce the Schiff's base and at the same time to stabilize the covalent bond, 0.5 ml of a freshly prepared aqueous 0.1 mol/l sodium borohydride solution is admixed with the avidin-peroxidase solution, whereupon the mixture is incubated at 2°–8° C. for at least 2 hours. The avidin-peroxidase conjugate is subsequently dialyzed against phosphate-buffered physiological sodium chloride solution with 0.66 mg/l of Merfen and stabilized with 10 mg/l of bovine serum albumin.

In order to form the complex, 55 μl of anti-CEA (C-3) antibody-biotin conjugate are mixed with 48 μl of avidin-peroxidase conjugate and the mixture is incubated at room temperature for 15 minutes.

For use in accordance with the invention, the complex is diluted with a solution containing 0.20 mol/l or 0.80 mol/l of sodium phosphate buffer of pH 6.5, 2 g/l of bovine serum albumin, 20% of goat serum and 0.1 g/l of 4-amino-antipyrine.

We claim:

1. In a solid phase-sandwich method for the rapid determination of carcino-embryonic antigen (CEA) which comprises incubating a sample to be investigated with a first CEA antibody, which is bound to or becomes bound to a water-insoluble carrier, and a second CEA antibody, to which peroxidase is bound directly or via a biotin/avidin bridge, separating the solid and liquid phase and measuring of the peroxidase activity either in the solid or in the liquid phase as the amount of CEA present, wherein the improvement comprises carrying out the incubation in the presence of 0.4–1.0 mol/l of phosphate ions, of 0.2–0.4 mol/l of sulfate ions or of 0.2–0.4 mol/l of tartrate ions.

2. The method according to claim 1, wherein the sample is incubated with the first CEA antibody, which is bound to or becomes bound to a water-insoluble carrier, and, after a washing step, is incubated with the second CEA antibody, to which peroxidase is bound directly or via a biotin/avidin bridge, whereby the second incubation is carried out in the presence of 0.4–1.0 mol/l of phosphate ions, of 0.2–0.4 mol/l of sulfate ions or of 0.2–0.4 mol/l of tartrate ions.

3. The method according to claim 1 or claim 2, wherein the peroxidase is bound directly to the second CEA antibody.

4. The method according to claim 3, wherein the two CEA antibodies are obtained from antiserum of different animal species and wherein peroxidase is bound directly to one of the antibodies.

5. The method according to claim 4, wherein CEA antibodies from goat and guinea pig are used and wherein in the peroxidase is bound directly to the goat antibody.

6. The method according to claim 1 or claim 2, wherein two different monoclonal mouse-CEA antibodies are used and wherein the peroxidase is bound to one of the monoclonal antibodies via a biotin/avidin bridge.

7. The method according to claim 3, wherein there is used a CEA antibody, which is obtained from an antiserum of an animal, as well as a monoclonal mouse-CEA antibody and wherein the peroxidase is bound directly to the antibody obtained from an antiserum.

8. The method according to claim 7, wherein as the CEA antibodies there are used goat-CEA antibody and monoclonal mouse-CEA antibody and wherein the peroxidase is bound directly to the goat-CEA antibody.

9. CEA antibody, to which peroxidase is coupled directly or via a biotin/avidin bridge, in an aqueous solution of pH 4–9, wherein the solution contains 0.4–1.0 mol/l of phosphate ions, 0.2–0.4 mol/l of sulfate ions or 0.2–0.4 mol/l of tartrate ions.

10. CEA antibody according to claim 9, wherein the peroxidase is coupled directly to the antibody.

11. A test kit for determining carcinoembryonic antigen (CEA) in a sample, comprising:
    (a) a first CEA antibody which is bound to water-insoluble carrier;
    (b) a second CEA antibody labeled with peroxidase wherein the peroxidase is bound directly or via a biotin/avidin bridge;
    (c) an aqueous solution of pH 4–9 comprising 0.4–1.0 mol/l of phosphate ions, 0.2–0.4 mol/l of sulfate ions or 0.2–0.4 mol/l of tartrate ions.

12. The test kit according to claim 11, wherein the two CEA antibodies are obtained from antiserum of different animal species and wherein the peroxidase is bound directly to one of the antibodies.

13. A test kit according to claim 11, wherein CEA antibodies from goat and guinea pig are used and wherein the peroxidase is bound directly to the goat antibody.

14. The test kit according to claim 11, wherein two different monoclonal mouse-CEA antibodies are used and wherein the peroxidase is bound to one of the monoclonal antibodies via a biotin/avidin bridge.

15. The test kit according to claim 11, wherein there is used a CEA antibody, which is obtained from an antiserum of an animal, as well as a monoclonal mouse-CEA antibody and wherein the peroxidase is bound directly to the antibody obtained from an antiserum.

16. The test kit according to claim 11, wherein as the CEA antibodies there are used goat-CEA antibody and monoclonal mouse-CEA antibody and wherein the peroxidase is bound directly to the goat-CEA antibody.

* * * * *